(12) United States Patent
Veenstra et al.

(10) Patent No.: US 8,722,037 B2
(45) Date of Patent: May 13, 2014

(54) X-RAY VISIBLE DRUG DELIVERY DEVICE

(75) Inventors: Harm Veenstra, Oss (NL); Wouter De Graaff, Oss (NL)

(73) Assignee: Meck Sharp & Dohme B.V., BN Harleem (NL)

( * ) Notice: Subject to any disclaimer, the term of this patent is extended or adjusted under 35 U.S.C. 154(b) by 1383 days.

(21) Appl. No.: 10/592,725

(22) PCT Filed: Mar. 14, 2005

(86) PCT No.: PCT/EP2005/051150
§ 371 (c)(1),
(2), (4) Date: Oct. 6, 2006

(87) PCT Pub. No.: WO2005/089814
PCT Pub. Date: Sep. 29, 2005

(65) Prior Publication Data
US 2008/0112892 A1      May 15, 2008

(30) Foreign Application Priority Data

Mar. 19, 2004   (EP) .................................. 04101151

(51) Int. Cl.
*A61K 38/43*          (2006.01)
*A61F 2/00*           (2006.01)

(52) U.S. Cl.
USPC ........................................ 424/94.1; 424/423

(58) Field of Classification Search
USPC .............................................. 424/94.11, 423
See application file for complete search history.

(56) References Cited

U.S. PATENT DOCUMENTS

| 4,866,132 | A |   | 9/1989  | Obligin et al.           |
|-----------|---|---|---------|--------------------------|
| 4,957,119 | A | * | 9/1990  | de Nijs ............ 128/832 |
| 5,150,718 | A |   | 9/1992  | De Nijs                  |
| 6,162,236 | A | * | 12/2000 | Osada ............. 606/185 |
| 6,371,094 | B1|   | 4/2002  | Wagner                   |
| D551,759  | S |   | 9/2007  | Tak et al.               |
| 7,378,477 | B2| * | 5/2008  | Hurtevent et al. ..... 526/287 |
| 7,553,352 | B2|   | 6/2009  | Stinson                  |
| 2001/0003297 | A1 |   | 6/2001 | Pedersen et al. |
| 2001/0031940 | A1 |   | 10/2001| Loos            |
| 2003/0010929 | A1 | * | 1/2003 | Priewe et al. ...... 250/443.1 |
| 2003/0059371 | A1 |   | 3/2003 | Matson et al. ........... 424/9.3 |
| 2003/0153983 | A1 | * | 8/2003 | Miller et al. .......... 623/23.7 |
| 2008/0221510 | A1 |   | 9/2008 | Van Der Graaf   |
| 2009/0012463 | A1 |   | 1/2009 | Beelen          |

FOREIGN PATENT DOCUMENTS

| DE | 35 13928 A1 | 10/1985 |
| DE | 299 08 415 U1 | 9/1999 |
| EP | 0 073 308 A1 | 3/1983 |
| EP | 0 303 306 A1 | 2/1989 ............... A61K 9/70 |
| EP | 0 304 107 | 2/1989 |
| EP | 0303306 B1 | 3/1993 |
| EP | 0 631 794 | 6/1994 |
| EP | 0 938 894 A1 | 9/1999 |
| EP | 1 053 747 B1 | 11/2000 |
| EP | 0 824 900 B1 | 4/2003 |
| EP | 0894503 B1 | 12/2006 |
| EP | 1 729 819 B1 | 7/2008 |
| GB | 2 168 257 A | 6/1986 ............... A61F 5/47 |
| GB | 2 285 981 A | 8/1995 |
| JP | 1-178540 A | 7/1999 |
| JP | 2002-360685 A | 12/2002 |
| WO | 96/26682 A1 | 9/1996 |
| WO | WO 98/58698 | 12/1998 |
| WO | 99/24391 A1 | 5/1999 |
| WO | 99/29260 A2 | 6/1999 |
| WO | 99/29260 A3 | 6/1999 |
| WO | 00/12016 A1 | 3/2000 |
| WO | 01/34196 A2 | 5/2001 |
| WO | 01/34196 A3 | 5/2001 |
| WO | 01/49340 A1 | 7/2001 |
| WO | 01/56646 A1 | 8/2001 |
| WO | WO 01/68168 | 9/2001 |
| WO | 02/41929 A1 | 5/2002 |
| WO | 02/076525 A1 | 10/2002 |
| WO | 03/051335 A1 | 6/2003 |
| WO | WO 2004/011055 A2 | 2/2004 ............. A61L 31/00 |
| WO | WO 2004/011055 A3 | 2/2004 ............. A61L 31/00 |
| WO | WO 2004/020011 A1 | 3/2004 |
| WO | WO 2004/089458 | 10/2004 |
| WO | WO 2006/077250 | 7/2006 |

OTHER PUBLICATIONS

Gould et al, Use of Intrauterine Devices (IUDs) or Contraception in the Common Chimpanzee, J Med Primatol 2000: 29: 63-69.*
Chikamata et al, Health Services at the Clinical Level and Implantable Contraceptives for Women, Contraception 65 (2002) 97-106.*
International Search Report for International Application No. PCT/2005/051150 dated Aug. 2, 2005.
Written Opinion for International Application No. PCT/EP2005/051150.
Taghizadeh, S.M., et al. "Study of Progesterone Release Mechanisms from a Silicone Matrix by a New Analytical Method", Journal of Applied Polymer Science, (2004), pp. 3040-3044, vol. 91.
van Laarhoven, et al., "Effect of supersaturation and crystallization phenomena on the release properties of a controlled release device based on EVA copolymer", *Journal of Controlled Release* (2002) 82: 309-317.
A.P. Sam, "Controlled release contraceptive devices: a status report", *Journal of Controlled Release* (1992) 22: 35-46.
Aguilar-De-Leyva, A. et al., "Release behaviour of clozapine matrix pellets based on percolation theory", International Journal of Pharmaceutics, 2011, p. 133-141, vol. 404.
Bonny, J. D. et al., "Matrix Tye Controlled Release Systems: I. Effect of Percolation on Drug Dissolution Kinetics", Pharm. Acta Helv, 1991, p. 160-164, vol. 66.
Bonny, J. D. et al., Matrix type controlled release systems: II. Percolation effects in non-swellable matrices, Pharmaceutica Acta Helvetiac, 1993, p. 25-33, vol. 68.

(Continued)

*Primary Examiner* — Brian-Yong Kwon
*Assistant Examiner* — Jennifer Berrios
(74) *Attorney, Agent, or Firm* — Janet E. Fair; Catherine D. Fitch

(57) ABSTRACT

The subject invention provides an X-ray visible drug delivery device for subdermal administration of a contraceptive or hormone replacement therapy.

24 Claims, 16 Drawing Sheets

(56) References Cited

OTHER PUBLICATIONS

Figure 1:
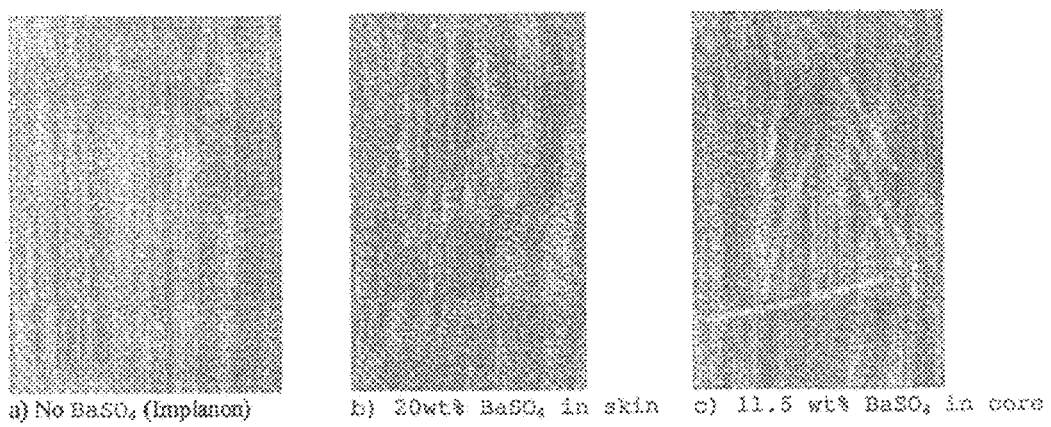

Boza, A. et al., "Application of a New Mathematical Method for the Estimation of the Mean Survace Area to Calculate the Percolation Threshold of Lobenzarit Dissodium Salt in Controlled Release Matrices", Chem. Phar. Bull, 2004, p. 797-801, vol. 52, No. 7.

Burns, R. et al., "A One Year Controlled Release Implant for the Luteinizing Hormone Releasing Hormone Superagonist RS-49947.I. Implant Characterization and Analysis of In Vitro Results", Journal of Controlled Release, 1990, p. 221-232, vol. 14.

Caraballo, I. et al., "Design of cotnrolled release inert matrices of naltrexone hydrochloride based on percolation concepts", International Journal of Pharmaceutics, 1999, p. 23-30, vol. 181.

Caraballo, I. et al., "Relationship Between Drug Percolation Threshold and Particle Size in Matrix Tablets", Pharmaceutical Research, 1996, p. 387-390, vol. 13, No. 3.

Di Colo, G. et al., "Controlled drug release from implantable matrices based on hydrophobic polymers", Biomaterials, 1992, p. 850-856, vol. 13, No. 12.

El-Arini, S. K. et al., "Modelling of drug release from polymer matrices: Effect of drug loading", International Journal of Pharmaceutics, 1995, p. 141-148, vol. 121.

Fernandez-Hervas, M. J. et al., "Percolation therory: Evaluation and interest of percolation thresholds determination in inert matrix tablets", Pharmaceutica Acta Helvetiae, 1996, p. 259-264, vol. 71.

Guo, Q. H. et al., "Estimation of 5-fluorouracil-loaded ethylene-vinyl acetate stent coating based on percolation thresholds", International Journal of Pharmaceutics, 2007, p. 95-102, vol. 333.

Hastedt, J. E. et al., "Diffusion on Porous Materials Above the Percolation Threshold", Pharmaceutical Research, 1990, p. 893-901, vol. 7. No. 9.

Leuenberger, H. et al., "Percolation effects in matrix-type controlled drug release systems", International Journal of Pharmaceutics, 1995, p. 217-224, vol. 115.

Melgoza, L. M. et al., "Estimation of the percolation thresholds in dextromethorphan hydrobromide matrices", European Journal of Pharmaceutical Sciences, 2001, p. 453-459, vol. 12.

Miranda, A. et al., "Investigation of the Influence of Particle Size on the Excipient Percolation Thresholds of HPMC Hydrophilic Matrix Tablets", Journal of Pharmaceutical Sciences, 2007, p. 2746-2756, vol. 96, No. 10.

Soriano, M. C. et al., "Influence of two different types of excipient on drug percolation threshold", International Journal of Pharmaceutics, 1998, p. 63-69, vol. 174.

International Search Report for International Application No. PCT/2005/051150, dated Aug. 2, 2005.

Written Opinion for International Application No. PCT/EP2005/051150, 2005.

International Preliminary Report on Patentability for International Application No. PCT/EP2005/051150 dated Jun. 27, 2006.

Merki-Feld, G. S. et al., "Nonpalpable ultrasonographically not detectable Implanon rods can be localized by magnetic resonance imaging", Contraception, 2001, p. 325-328, vol. 63.

* cited by examiner a) No BaSO₄ (Implanon)   b) 20wt% BaSO₄ in skin   c) 11.5 wt% BaSO₄ in core a) No wire (Implanon)   b) 0.5 mm wire

Figure 11

Sample no.: 1    2  3    4  5  6

Figure 15
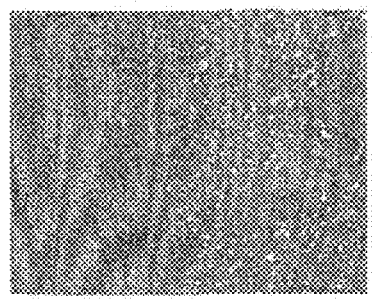
a) 4 wt% BaSO₄
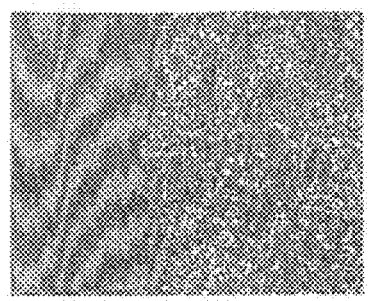
b) 20 wt% BaSO₄
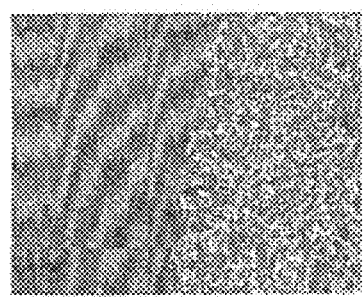
c) 30 wt% BaSO₄

Figure 16
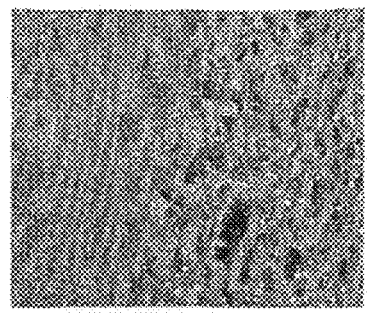
a) 4 wt% BaSO₄
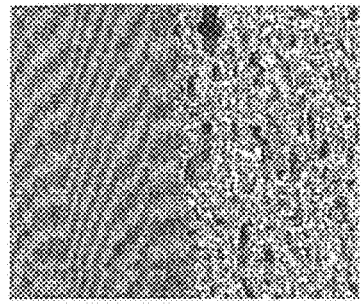
b) 20 wt% BaSO₄
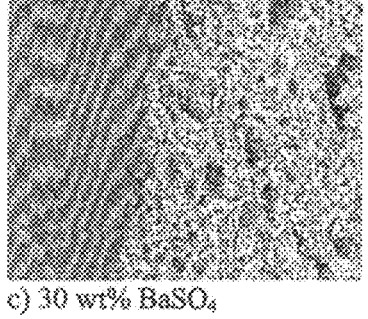
c) 30 wt% BaSO₄

X-RAY VISIBLE DRUG DELIVERY DEVICE

FIELD OF THE INVENTION

The present invention relates to the field of contraception and hormone replacement therapy.

The present invention relates to an X-ray visible drug delivery device for subdermal (subcutaneous) administration of a contraceptive or hormone replacement therapy.

The device according to the invention is particularly in the form of an implant, and will hereinafter be referred to as an implant.

BACKGROUND OF THE INVENTION

Implanon® is a contraceptive implant that is inserted in the human body for periods up to 3 years. Cases have been reported in which the implants could not easily be removed due to either incorrect insertions by physicians or due to non-insertion of the implant by physicians. Implanon can be visualized in the body using ultrasonography and MRI techniques. Visualization by MRI is not always readily available, relatively complicated and expensive. Visualization by ultrasonography is also not always readily available and may be difficult in the hands of inexperienced physicians especially in the event the implant was inserted incorrectly.

The implant should be removed (and replaced) after three years. Furthermore, women may want to remove the implant if they wish to become pregnant. Another reason for removal can be disease, such as cancer, especially breast cancer, ovary cancer or cancer of the uterus.

It would therefore be convenient to have an Implanon-like implant which will be X-ray visible. This in order to have additional methods to locate and identify the implant, either to facilitate removal of the implant or to be able to reassure the patient that the implant has been inserted.

Such a contemplated X-ray visible implant must be such that the radio-opaque component does not (i) influence the hormone release profile of the implant and (ii) does not migrate into the body through the open-ended implant.

X-ray visible medical devices, such as stents, catheters, intra-uterine devices such as MultiLoad®, biodegradable implants and dental devices are known. An X-ray visible drug delivery device known in the field of contraception is described in GB 2168257 which shows an X-ray visible vaginal ring comprising the progestogen levonorgestrel. GB2168257 does not relate to the influence of the radio-opaque component on the release rate of levonorgestrel from the ring, nor does such a ring have open-ends.

It is however crucial to ascertain that the hormone release rate is not significantly affected by a radio-opaque component present in the contraceptive device because that could possibly result in pregnancy, the unwanted effect for a woman using contraception.

Moreover, it is also crucial that a radio-opaque component present in the contraceptive/HRT device does not migrate outside the (open-ended) implant into the body in undesired amounts causing potential radio-opaque component related adverse effects.

Thus, the subject invention provides for a contraceptive and/or HRT X-ray visible implant wherein the radio-opaque component does not negatively influence the release rate of hormones from the device and does not migrate into the body.

SUMMARY OF THE INVENTION

The subject invention provides an X-ray visible drug delivery device for subdermal administration of a contraceptive or hormone replacement therapy comprising one compartment consisting of (i) a thermoplastic polymer core loaded with (a) a contraceptively effective or therapeutically effective amount of desogestrel or 3-ketodesogestrel and (b) about 4-30% by weight radio-opaque material and (ii) a non-medicated thermoplastic polymer skin covering the core.

The subject invention further provides an X-ray visible drug delivery device for subdermal administration of a contraceptive or hormone replacement therapy comprising one compartment consisting of (i) a thermoplastic polymer core loaded with a contraceptively effective or therapeutically effective amount of desogestrel or 3-ketodesogestrel and containing an inert metal wire and (ii) a non-medicated thermoplastic polymer skin covering the core.

FIGURES

FIG. 1: X-ray photographs of implants a) without barium sulphate ($BaSO_4$)(i.e. identical to Implanon); b) with 20 wt % $BaSO_4$ in skin; and c) with 11.5 wt % $BaSO_4$ in core.

Figure 2:
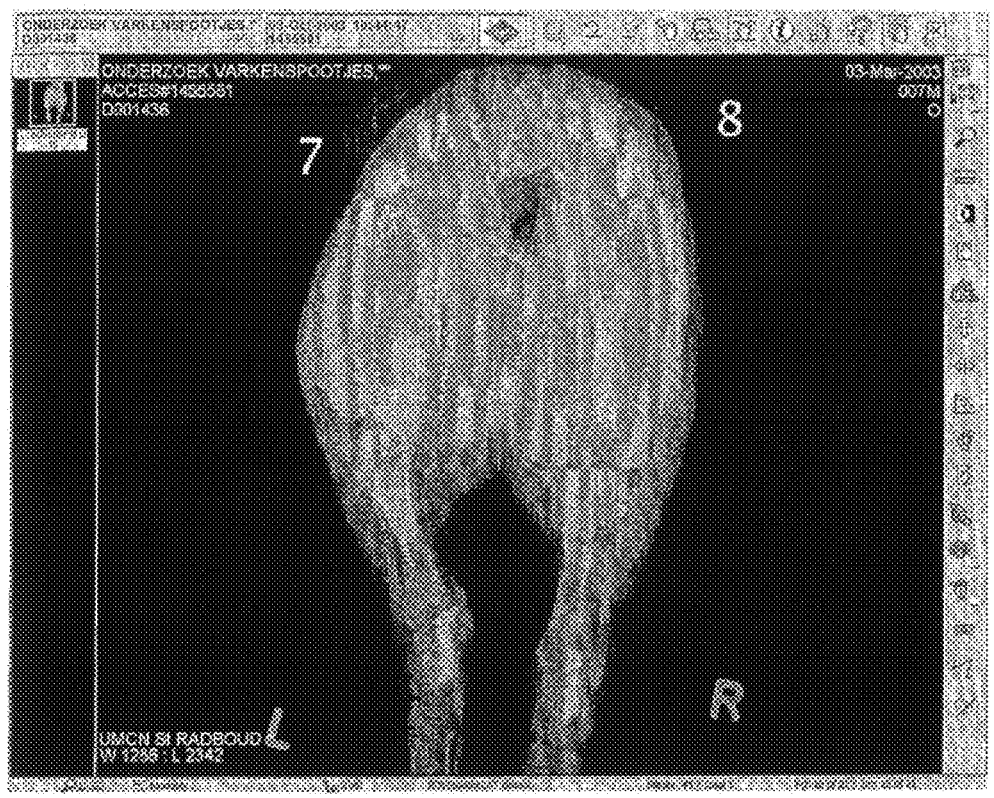

FIG. 2: X-ray photographs of implants without barium sulphate (sample 8) and with 11.5 wt % $BaSO_4$ in core (sample 7) inserted in pig tissue.

Figure 3:
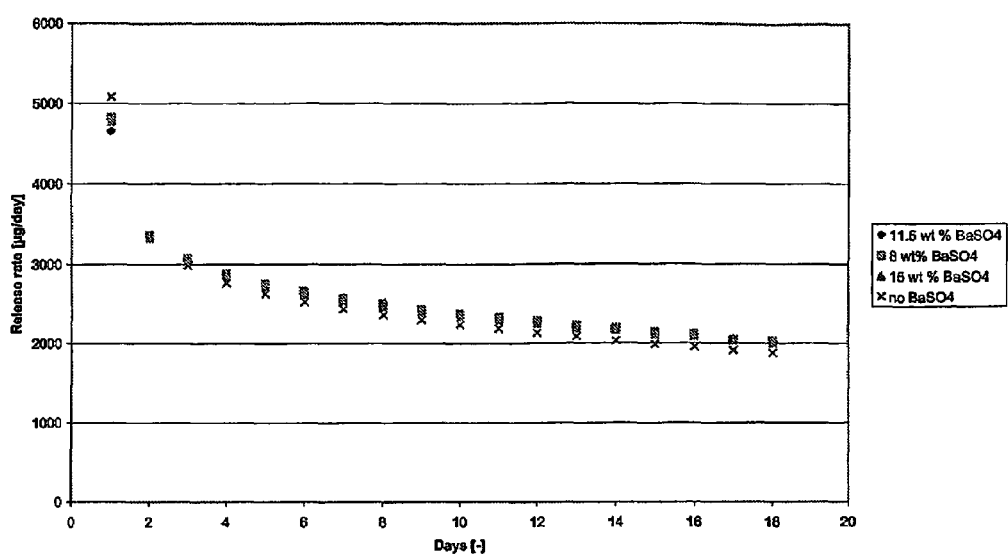

FIG. 3: Accelerated release profiles of implants with 0, 8, 11.5 and 15 wt % barium sulphate in the core. (The implant with 0 wt % is identical to Implanon.)

Figure 4:
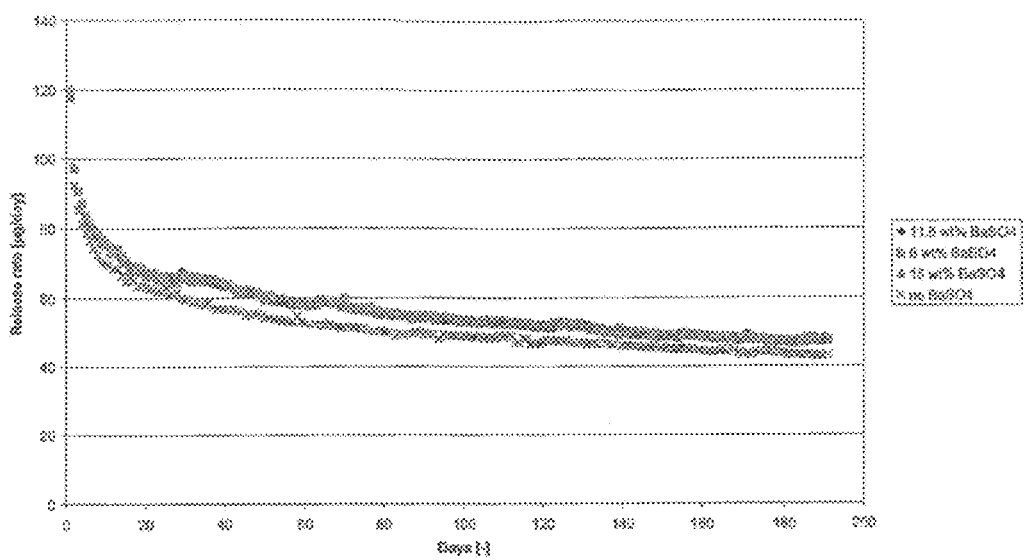

FIG. 4: Real time release profiles up to 190 days of implants with 0, 8, 11.5 and 15 wt % barium sulphate in the core. (The implant with 0 wt % is identical to Implanon).

Figure 5:
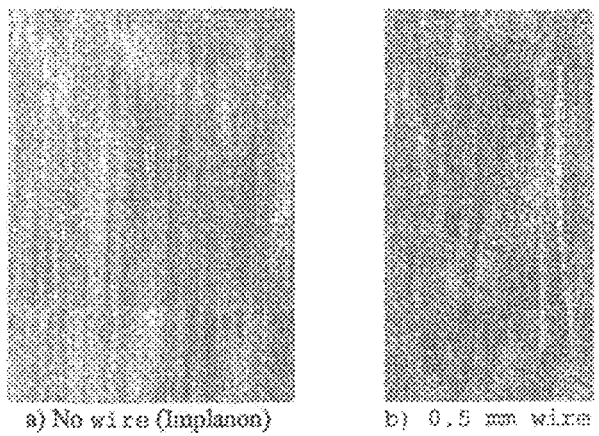

FIG. 5: X-ray photographs of implants a) without $BaSO_4$ or titanium wire (i.e. identical to Implanon); and b) with 0.5 mm titanium wire.

Figure 6:
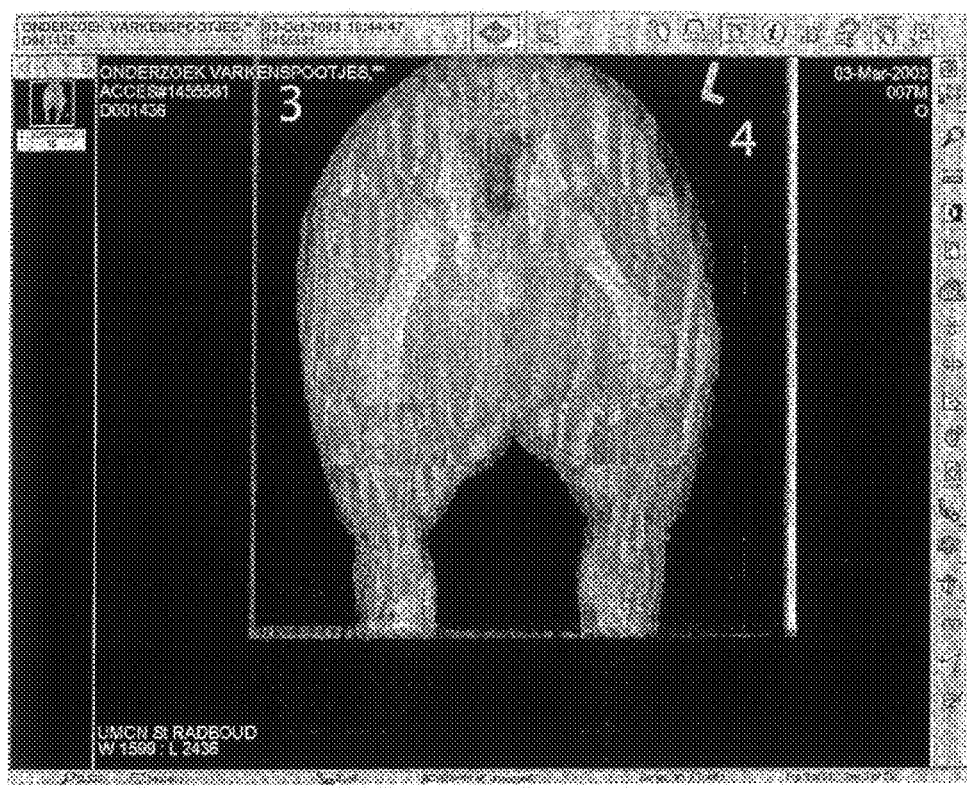

FIG. 6: X-ray photographs of implants without titanium wire (sample 3) and with a 0.5 mm titanium wire in the core (sample 4) inserted in pig tissue.

Figure 7:
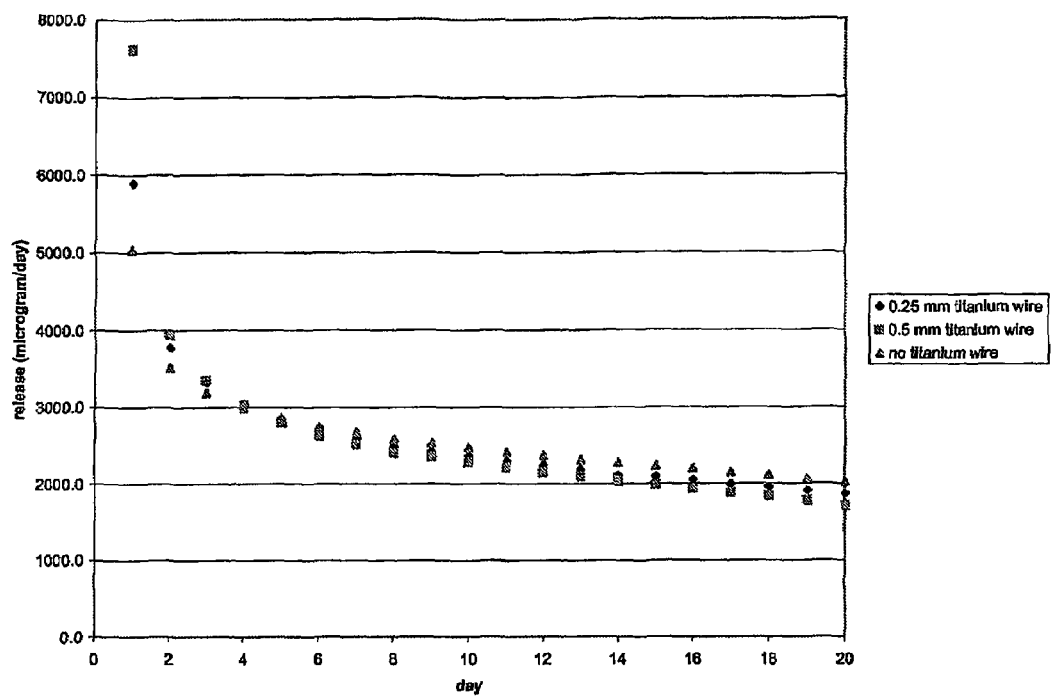

FIG. 7: Accelerated release profiles of implants with a 0.25 mm titanium wire in the core, a 0.50 mm titanium wire in the core and a reference implant (identical to Implanon) with no titanium wire.

Figure 8:
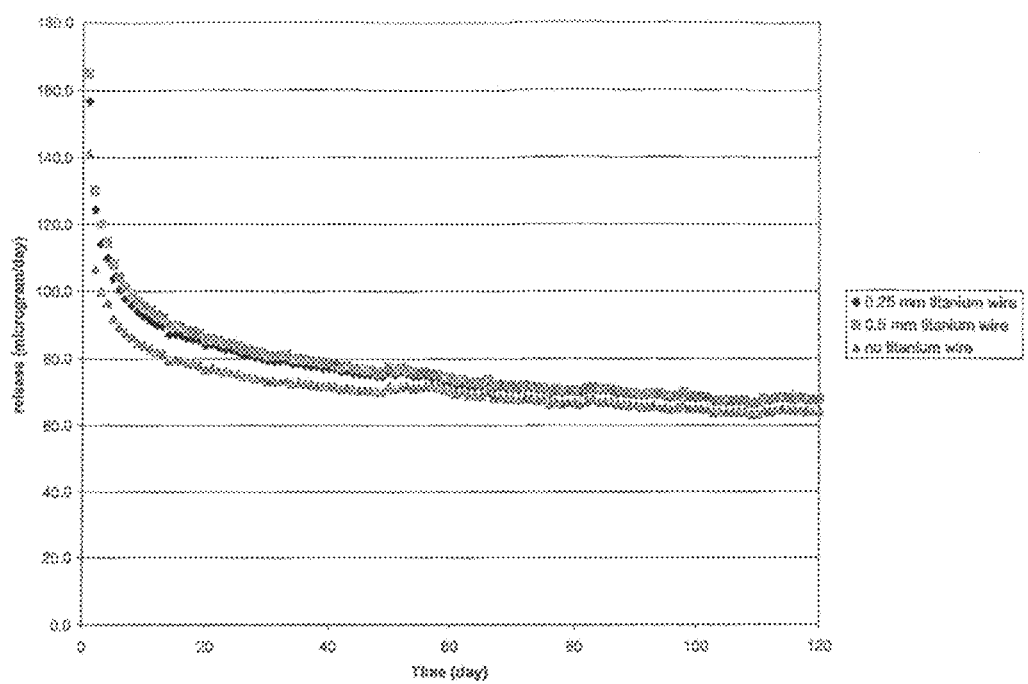

FIG. 8: Real time release profiles of implants with a 0.25 mm titanium wire in the core, a 0.50 mm titanium wire in the core and a reference implant (identical to Implanon) with no titanium wire.

Figure 9:
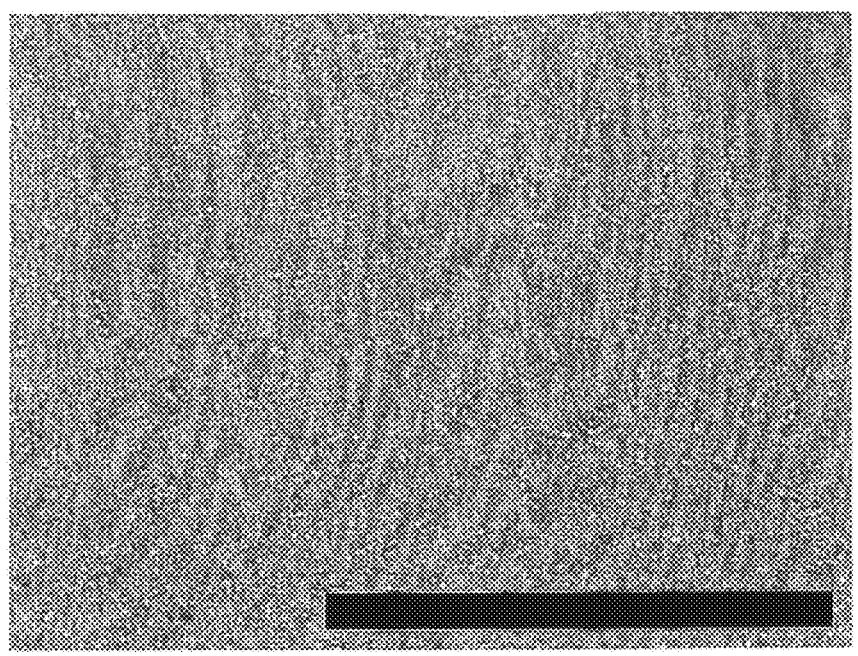

FIG. 9: Back Scatter Electron (BSE) detector photograph (magnification 350×) of implant with 11.5 wt % barium sulphate in the core FIG. 10: BSE detector photograph (magnification 3500×) of leached implant with 11.5 wt % barium sulphate in the core. The dark section on the left is the skin.

Figure 11:
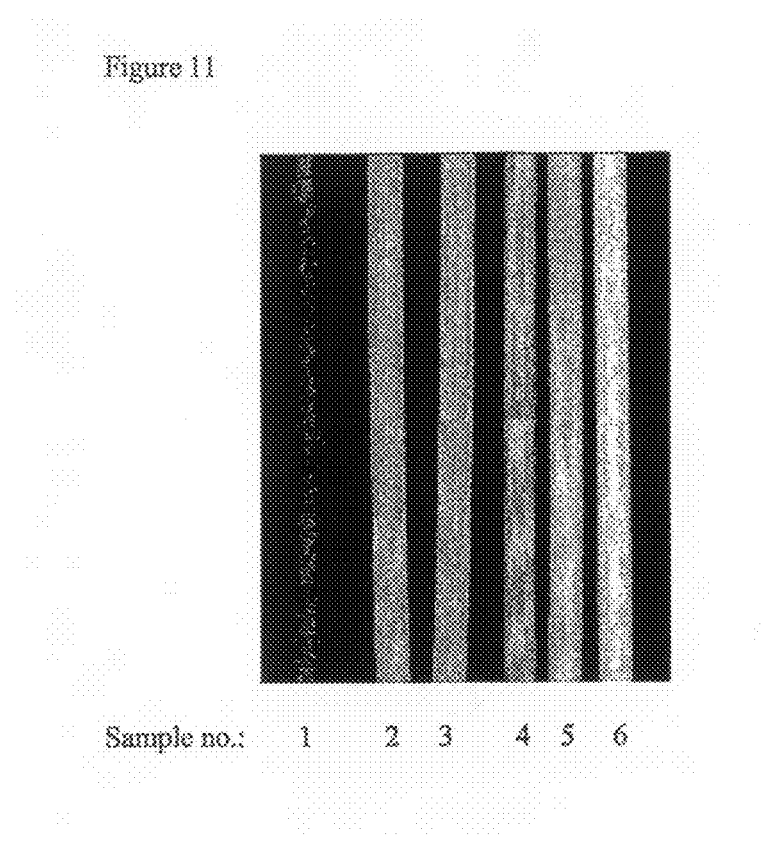

FIG. 11: X-ray photographs of implants a) without $BaSO_4$ (i.e. identical to Implanon, sample 1); b) with 11.5 wt % $BaSO_4$ in core (samples 2 and 3); c) with 4 wt % $BaSO_4$ in core; d) with 20 wt % $BaSO_4$ in core; and e) with 30 wt % $BaSO_4$ in core.

Figure 12:
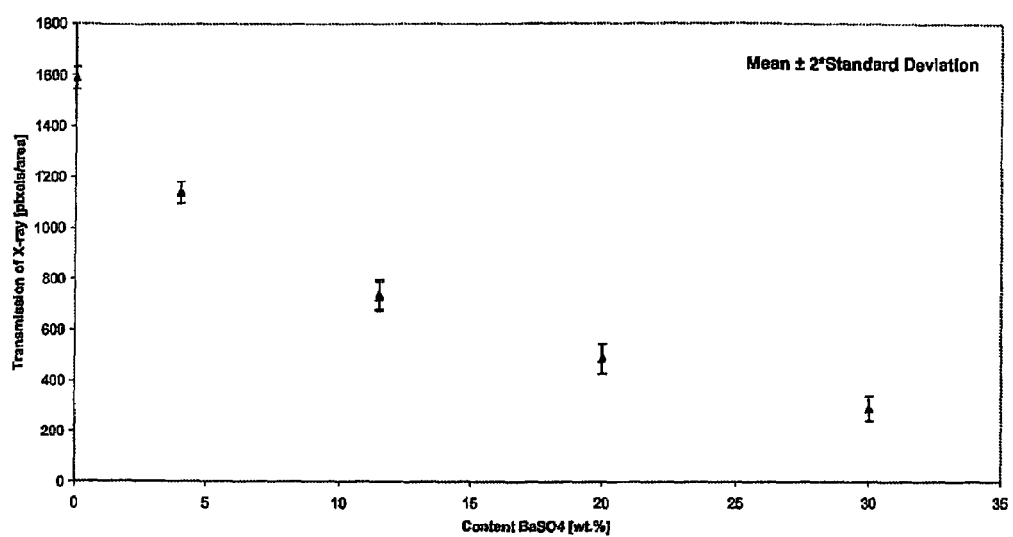

FIG. 12: X-ray transmission of implants as function of content $BaSO_4$(wt (%)).

Figure 13:
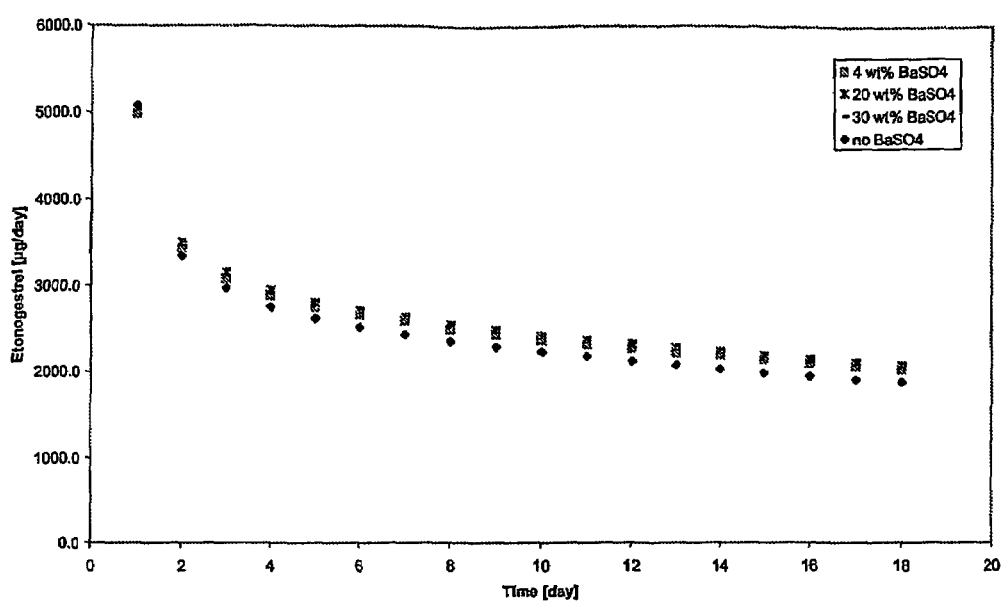

FIG. 13: Accelerated release profiles of implants with 0, 4, 20 and 30 wt % barium sulphate in the core. (The implant with 0 wt % is identical to Implanon.)

Figure 14:
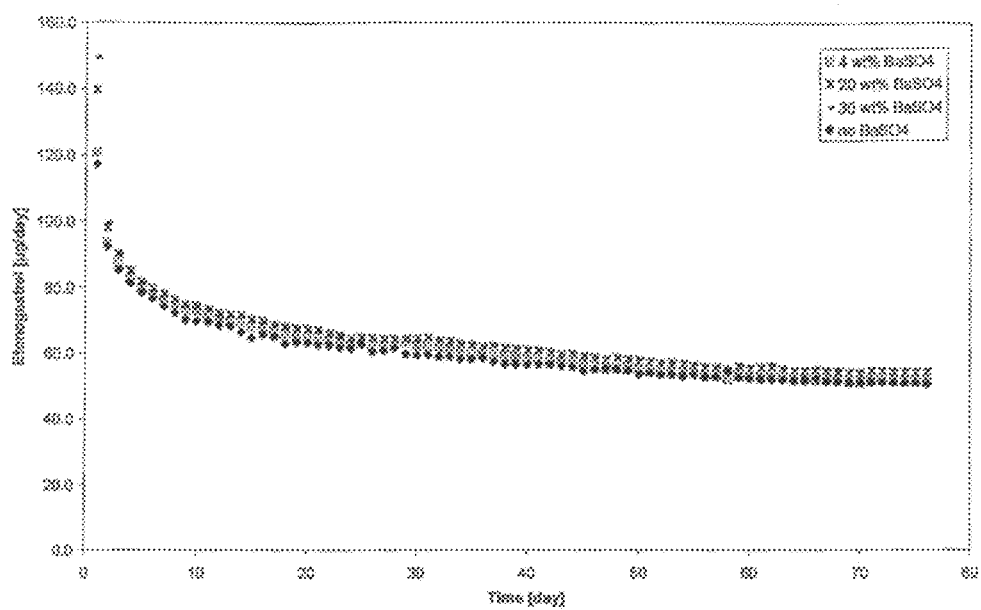

FIG. 14: Real time release profiles up to 76 days of implants with 0, 4, 20 and 30 wt % barium sulphate in the core. (The implant with 0 wt % is identical to Implanon).

FIG. 15: Back Scatter Electron (BSE) detector photograph (magnification 350×) of implant with a) 4 wt % barium sulphate in the core; b) 20 wt % barium sulphate in the core; and c) 30 wt % barium sulphate in the core.

FIG. 16: BSE detector photograph (magnification 3500×) of leached implant with a) 4 wt % barium sulphate in the core; b) 20 wt % barium sulphate in the core; and c) 30 wt % barium sulphate in the core. The dark section on the left is the skin.

DETAILED DESCRIPTION OF INVENTION

Implanon® is a subdermal contraceptive implant consisting of a coaxial rod. The core of this rod contains a mixture of etonogestrel (3-keto desogestrel) and ethylene vinylacetate (EVA) copolymer, i.e. EVA 28 which has a vinylacetate content of about 28% (m/m). The skin layer also consists of EVA polymer, i.e. EVA 14, which has a vinyl acetate content of about 14% (m/m). Each rod has a mass of 129 mg and contains 68 mg etonogestrel. Implanon has a length of 40 mm and a diameter of 2 mm and has open ends.

The implant may be placed within an applicator consisting of a stainless steel needle, which is fitted to an acrylonitrile-butadiene-styrene polymer (ABS) applicator. The applicator is a syringe-like apparatus consisting of a body, plunger, needle and polypropylene shield. The loaded applicator may be placed in a polyethylene terephthalate glycol (PETG) tray, which may be subsequently sealed with lidding paper.

The object of the invention is to add a radio-opaque element to a contraceptive/HRT implant such as Implanon® providing the possibility to identify and locate it in the body by X-ray techniques while maintaining the hormone release profile thereof and while ensuring that the radio-opaque component does not migrate outside of the implant in undesired amounts into the body.

One skilled in the art will appreciate that a hormone release profile of a batch of a drug delivery device is never exactly identical to another batch of the same drug delivery device. Therefore, according to the subject invention, when the hormone release profile of an X-ray visible implant of the invention deviates less than about 15% from the hormone release profile of Implanon®, these hormone release profiles are considered identical or equivalent. The deviation can be calculated using a difference factor ($F_1$) to compare dissolution profiles. The difference factor ($F_1$) calculates the percentage difference between two curves at each time point $$F_1 = \left\{ \left[ \sum_{t=1}^{n} |R_t - T_t| \right] / \left[ \sum_{t=1}^{n} R_t \right] \right\} * 100$$

Where $R_t$ is the reference assay at time point t, $T_t$ is the test assay at time point t and n is the number of pull points. F1 values up to 15 (0-15) provide assurance of the sameness or equivalence of the two curves. The reference curve is chosen such that other release controlling parameters, than the one that is tested, are kept as constant as possible.

When incorporating a radio-opaque element in the skin layer of the implant, X-ray visibility was hardly accomplished. However, X-ray visibility was accomplished when incorporating the radio-opaque element in the core of the implant. Despite the incorporation of the radio-opaque element in the core of the implant which also contains the active hormone material, the hormone release profile was not affected.

When evaluating where the radio-opaque component was located in the implant after production thereof, it was surprisingly found that almost all of the radio-opaque component was encapsulated within the polymer component and hardly any radio-opaque component was encapsulated in the hormone crystals. This was unexpected in view of the fact that the polymer component represents only about 36 wt % of the implant whereas the hormone component comprises about 52.5 wt % of the implant. As a result of the encapsulation within the polymer component, the radio-opaque component crystals could not migrate out of the implant through the open ends of the implant in undesired amounts. Had the radio-opaque component been present in the hormone crystals, it may have been able to migrate outside of the implant in case where the hormone crystals are inter-connected.

Thus, the subject invention provides an X-ray visible drug delivery device for subdermal administration of a contraceptive or hormone replacement therapy comprising one compartment consisting of (i) a thermoplastic polymer core loaded with (a) a contraceptively effective or therapeutically effective amount of desogestrel or 3-ketodesogestrel and (b) about 4-30% by weight radio-opaque material and (ii) a non-medicated thermoplastic polymer skin covering the core.

In one specific embodiment, the X-ray visible drug delivery device is an implant The radio-opaque element can be any such element known in the art such as barium sulphate, titanium oxide, bismuth oxide, tantalum, tungsten, or platinum. In a specific embodiment, the radio-opaque material is barium sulphate.

In one embodiment, the radio-opaque material is about 4-25% by weight. In another embodiment, the radio-opaque material is about 6-20% by weight. In yet another embodiment, the radio-opaque material is about 4-15% by weight. In a specific embodiment, the radio-opaque material is about 8-15% by weight.

The thermoplastic polymer that can be used in practicing the invention, may in principle be any thermoplastic polymer or elastomer material suitable for pharmaceutical use, such as low density polyethylene, ethylene-vinylacetate copolymers and styrene-butadiene-styrene copolymers. In a specific embodiment, ethylene-vinylacetate copolymer (poly-EVA) is used due to its excellent mechanical and physical properties (e.g. solubility of the steroids in the material). The poly-EVA material may be used for the core as well as the skin and can be any commercially available ethylene-vinylacetate copolymer, such as the products available under the trade names: Elvax, Evatane, Lupolen, Movriton, Ultrathene, Ateva and Vestypar.

The radio-opaque material in the core does not affect the release of the desogestrel or 3-ketodesogestrel from the device and does not migrate out of the implant.

The subject invention further provides an X-ray visible drug delivery device for subdermal administration of a contraceptive or hormone replacement therapy comprising one compartment consisting of (i) a thermoplastic polymer core loaded with a contraceptively effective or therapeutically effective amount of desogestrel or 3-ketodesogestrel and containing an inert metal wire and (ii) a non-medicated thermoplastic polymer skin covering the core.

The radio-opaque element may be an inert titanium wire or other inert material such as certain grades of stainless steel or gold alloys. In a specific embodiment, the inert metal wire is a titanium wire.

The metal wire in the core does not affect the release of the desogestrel or 3-ketodesogestrel from the device.

The present invention is further described in the following examples which are not in any way intended to limit the scope of the invention as claimed.

EXAMPLES

Example 1

Preparation of Two-Layered Implant Containing Barium Sulphate in the Core

Preparation of two layered implant containing barium sulphate in the core consisted of two steps, i.e. manufacturing of core granulate (pre-mixing and blend extrusion) containing a mixture of etonogestrel (3-keto desogestrel), barium sulphate and EVA-28 copolymer and manufacturing of a co-axial fiber consisting of the core and a skin layer of EVA-14 copolymer.

The core material was prepared by adding the desired amount (e.g. 52.5 wt % etonogestrel, 36 wt % EVA, 11.5 wt % Barium sulphate) of ingredients to a stainless steel drum after which the powder mixture was pre-mixed by rotating the drum on a rhönrad, or equivalent, at 47 rpm. The powder mixture was subsequently fed to a Berstorff ZE25 co-rotating twin screw extruder (or equivalent) and blend extruded at an extrusion temperature of 125° C. Blend extrusion resulted in strands in which etonogestrel (3-keto desogestrel) and barium sulphate were homogeneously dispersed in the EVA-28 matrix. The strands were subsequently granulated to core granulate.

The co-extrusion set-up consisted of a skin extruder that processed the skin material and a core extruder that processed the core material as delivered by the blend extruder. The melt flows were combined in a spinneret resulting in a skin-core fibre. The volume flow rate of both melt flows was controlled by a set of separate spinning pumps. An extrusion temperature of 145° C. and an extrusion rate of 1 m/min was used. Extrusion lead to a co-axial fiber with a diameter of 2 mm and a skin thickness of 60 µm. The fiber was cooled down to room temperature in a water bath, dried on air and wound on a reel. The coaxial fiber was cut into 4.0 cm rods using a semi-automatic cutter (Diosynth or equivalent).

Example 2

Preparation of Two Layered Implant Containing Barium Sulphate in the Skin

Preparation of two layered implant containing barium sulphate in the skin consisted of three steps, i.e. manufacturing of core granulate (pre-mixing and blend extrusion) containing a mixture of etonogestrel (3-keto desogestrel) and EVA-28 copolymer, manufacturing of skin granulate (pre-mixing and blend extrusion) containing a mixture of Barium sulphate and EVA-14 copolymer, and manufacturing of a co-axial fiber consisting of the core and a skin layer.

The core material (e.g 60 wt % etonogestrel and 40 wt % EVA-28) and skin material (e.g. 20 wt % barium sulphate and 80 wt % EVA-14) were prepared by adding the desired ingredients to a stainless steel drum after which the powder mixtures were premixed by rotating the drum on a rhönrad, or equivalent, at 47 rpm.

The core powder mixture was subsequently fed to a Berstorff ZE25 co-rotating twin screw extruder (or equivalent) and blend extruded at an extrusion temperature of 125° C. Blend extrusion resulted in strands in which etonogestrel (3-keto desogestrel) was homogeneously dispersed in the EVA-28 matrix. The strands were subsequently granulated to core granulate. Essentially the same process, except for a higher extrusion temperature of 150° C., was executed for the skin powder mixture resulting in strands in which barium sulphate was homogeneously dispersed in the EVA-14 matrix. The strands were subsequently granulated to skin granulate.

The co-extrusion set-up consisted of a skin extruder that processed the skin granulate as delivered by the blend extruder and a core extruder that processed the core granulate as delivered by the blend extruder. The melt flows were combined in a spinneret resulting in a skin-core fibre. The volume flow rate of both melt flows was controlled by a set of separate spinning pumps. Ail extrusion temperature of 120° C. and an extrusion rate of 1 m/min was used. Extrusion lead to a co-axial fiber with a diameter of 2 mm and a skin thickness of 60 µm. The fiber was cooled down to room temperature in a water bath, dried on air and wound on a reel. The coaxial fiber was cut into 4.0 cm rods.

Example 3

Comparison of X-Ray Visibility Between Implant Containing Barium Sulphate in the Core, Implant Containing Barium Sulphate in the Skin and Implant without Barium Sulphate (Implanon)

X-ray photographs were taken from implants and subsequently the X-ray visibility between implants having barium sulphate in either core or skin versus x-ray visibility of implants without barium sulphate (Implanon) were compared. FIG. 1 demonstrates that incorporation of barium sulphate in the skin layer hardly improved the x-ray visibility when compared to implants without barium sulphate. However, incorporation of barium sulphate into the core greatly improved the X-ray visibility of the implant.

The x-ray visibility of the implant with barium sulphate in the core was also tested in vivo in pig tissue. For this purpose implants having barium sulphate in the core and implants without barium sulphate (Implanon) were inserted in hind legs of pigs and subsequently X-ray photographs were taken. FIG. 2 demonstrates that the barium sulphate containing implant (sample 7) is clearly visible while the Implanon implant is not (sample 8).

Example 4

Hormone Release Profile of Implant Containing Barium Sulphate in the Core in Comparison to Hormone Release Profile of Commercially Available Implanon

In-vitro release rate profiles of the implants were tested by two methods. An accelerated release rate method was performed by testing the implant in an ethanol/water (90/10) solution. For the real time release rate method the in-vitro release profile was tested in water. For both tests the release profile of an implant containing barium sulphate in the core was compared to the profile of Implanon without barium sulphate.

Implants were manufactured loaded with 8, 11.5 and 15 wt % barium sulphate in the core. The resulting accelerated release profiles are shown in FIG. 3 which demonstrates that all release profiles are similar and that within the tested range of barium sulphate content of the core (0-15 wt %) the radio-opaque component does not influence the release of hormones from the device. The same conclusion can be drawn from the real time release profiles up to 190 days (FIG. 4), i.e. within the tested range of barium sulphate content of the core (0-15 wt %) the radio-opaque component does not influence the release of hormones from the device.

These conclusions were substantiated by calculating F1 values. The F1 values were calculated for both accelerated release rate profiles (up to and including 18 days) as real time release rate profiles (up to and including 190 days) taking the Implanon release profiles as reference. The results are given in Table 1. F1 values up to 15 (0-15) provide assurance of the sameness or equivalence of the two curves.

TABLE 1

F1 values for Implants loaded with 8, 11.5 and 15 wt % barium sulphate in the core

| barium sulphate (wt %) | Accelerated release | Real time release |
| --- | --- | --- |
| 8 | 3.3 | 9.8 |
| 11.5 | 2.4 | 9.7 |
| 15 | 2.1 | 8.7 |

Example 5

Preparation of an Implant Containing a Titanium Wire in the Core

To prepare implants in which the core contains an inert titanium wire, Implanon rods with a diameter of 2 mm were adapted such that a titanium wire could be inserted. This was done by carefully drilling a canal in the implants in longitudinal direction. Spiral drills (Guhring Spiralbohre, Germany) with a diameter of either 0.40 or 0.60 mm were applied. A 0.40 mm spiral drill was applied for the implants in which a 0.25 mm titanium wire was inserted, whereas a 0.60 mm drill was used for the implant in which a 0.50 mm titanium wire was inserted. After the canal was prepared, the titanium wire was carefully inserted taking in consideration that the wire did not penetrate the skin layer. After insertion, the wire was cut at the rod end using a sharp cutter.

Example 6

Comparison of X-Ray Visibility Between Implant Containing a Titanium Wire in the Core and Implant without a Titanium Wire (Implanon)

X-ray photographs were taken from implants and subsequently the X-ray visibility between implants having a titanium wire in the core was compared to implants without a titanium wire (Implanon). As demonstrated in FIG. 5, insertion of a titanium wire into the core greatly improved the X-ray visibility of the implant.

The x-ray visibility of the titanium wire implant was also tested in vivo in pig tissue. For this purpose implants having a titanium wire in the core and implants without a wire (Implanon) were inserted in hind legs of pigs and subsequently X-ray photographs were taken. FIG. 6 demonstrates that the titanium wire containing implant (sample 4) is clearly visible while the Implanon implant is not (sample 3).

Example 7

Hormone Release Profile of Implant Containing Titanium Wire in Core in Comparison to Hormone Release Profile of Commercially Available Implanon In-vitro release rate profiles of Implanon were determined by two methods. An accelerated release rate method was performed by testing the implant in an ethanol/water (90/10) solution. For the real time release rate method the in-vitro release profile was tested in water. For both tests the release profile of implants containing titanium wire in the core was compared to the profiles of Implanon without titanium wire. The resulting accelerated release profiles are shown in FIG. 7 which demonstrates that all release profiles are comparable to the Implanon reference implant and that within the tested range of titanium wire diameters (0.25-0.50 mm) the influence on the release of hormones from the device by the radio-opaque component is acceptable.

The same conclusions can be drawn form the real time release profiles up to 118 days (FIG. 8), i.e. that all release profiles are comparable to the Implanon reference implant and that within the tested range of titanium wire diameters (0.25-0.50 mm) the influence on the release of hormones from the device by the radio-opaque component is acceptable.

These conclusions were substantiated by calculating F1 values. The F1 values were calculated for both accelerated release rate profiles (up to and including 18 days) as real time release rate profiles (up to and including 118 days) talking the Implanon release profiles as reference. The results are given in Table 2. F1 values up to 15 (0-15) provided assurance of the sameness or equivalence of the two curves.

TABLE 2

F1 values for Implants loaded with 0.25 and 0.50 mm titanium wires

| Titanium wire (mm) | Accelerated release | Real time release |
| --- | --- | --- |
| 0.25 | 2.6 | 8.1 |
| 0.50 | 7.7 | 10.8 |

Example 8

Migration of Barium Sulphate Particles Out of Implant with Open Ends

To reveal the distribution of barium sulphate in the implant and to obtain an impression of the loss of barium sulphate particles upon leaching, cryogenic sections were made of implants using a ultramicrotome. Subsequently the sections of the implants were analyzed using Scanning Electron Microscopy/Energy Dispersed Xspectroscopy (SEM/EDX) before and after leaching. Leaching the implants leads to removal of the etonogestrel crystals from the implant. By examining before and after leaching information is obtained on the morphology of the barium sulphate/etonogestrel/EVA-28 mixture. A back scatter electron (BSE) detector was used for imaging. In the BSE image the presence of barium sulphate particles is easily recognized by the high brightness of the barium sulphate particles.

Figure 10:
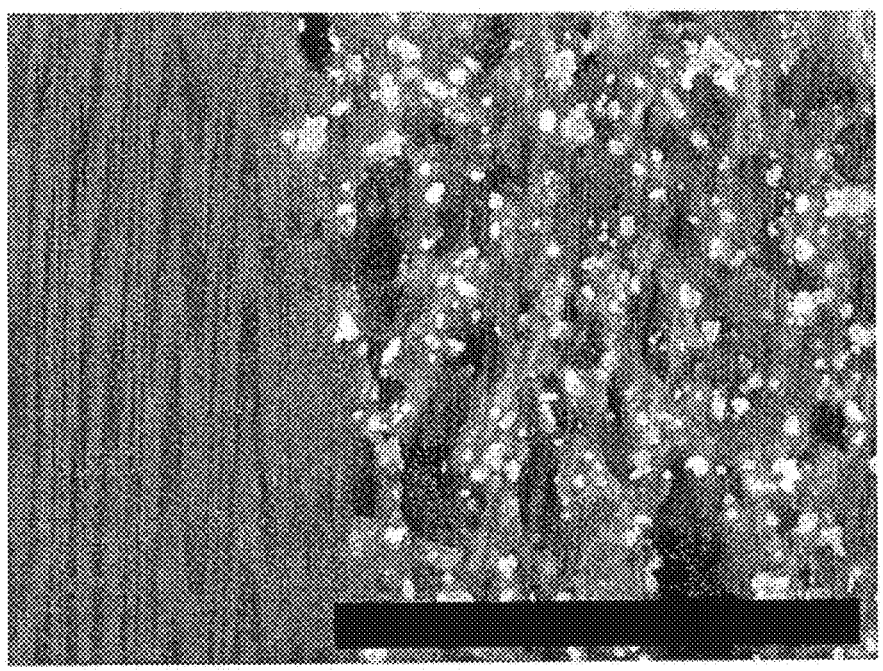

FIG. 9 reveals the morphology of an implant in which the core is loaded with about 11.5 wt % barium sulphate. It can be seen that the bright spots, representing barium sulphate, are mainly located in the EVA-28 material, i.e. the irregular shaped grey/black spots, representing etonogestrel crystals, contain no bright spots. FIG. 10 reveals the same sample that was leached. The left part is the skin material while the right part shows the leached core. Dark holes are clearly visible. The holes, representing the location at which etonogestrel crystals were present before leaching, hardly contain any bright spots.

The content barium sulphate in several batches was also tested using incineration before and after leaching (18 days in ethanol/water (90/10)). This gives information on possible migration of barium sulphate crystals out of the implant after the etonogestrel crystals were leached out of the implant. The results (table 3) show that there is no major change in content of barium sulphate upon leaching. It can therefore be concluded that no or hardly any barium sulphate crystals migrated out of the implant through the open ends.

Combining FIGS. 9 and 10 with the results in table 3 it can be concluded that hardly any radio-opaque component (shown by the bright spots) was encapsulated by the hormone crystals and that most of the radio-opaque component was encapsulated by the polymer EVA-28.

TABLE 3

Remnant content $BaSO_4$ of implants (average is given and range of 6 samples is given in brackets)

| Batch | untreated [mg $BaSO_4$/implant] | Leached (18 days $EtOH/H_2O$) [mg $BaSO_4$/implant] |
|---|---|---|
| Core with 11.5 wt % $BaSO_4$ | 14.7 (14.5-14.8) | 14.9 (14.7-15.1) |
| Core with 8 wt % $BaSO_4$ | 10.3 (10.2-10.4) | 9.5 (9.4-9.6) |
| Core with 15 wt % $BaSO_4$ | 19.7 (19.4-20.1) | 19.5 (19.4-19.6) |

Example 9

Comparison of X-Ray Visibility Between Implant Containing Barium Sulphate in the Core, and Implant without Barium Sulphate (Implanon)

X-ray photographs (at 26 KW and 0.6 mAs) were taken from implants and subsequently the X-ray visibility between implants having barium sulphate in the core versus x-ray visibility of implants without barium sulphate (Implanon) were compared FIG. 11 demonstrates that incorporation of barium sulphate into the core greatly improved the X-ray visibility of the implant. The implant with only 4 wt % barium sulphate content in the core (sample 4) is clearly visible while the Implanon (sample 1) implant without the barium sulphate is not.

The measured transmission of X-ray is a quantitative value for the X-ray visibility of the implants. The number represents the X-ray exposure (pixels per area) of a X-ray camera (transmission X-rays). Table 4 and FIG. 12 show that the amount of X-ray transmission of the implant with a low barium sulphate content in the core of 4 wt % (sample 4) is significantly different from the implant without $BaSO_4$ (sample 1).

TABLE 4

X-ray visibility of implant with and without $BaSO_4$

| Sample no. | $BaSO_4$ content [wt. %] | Transmission of X-ray [pixels/area] Mean [n = 4] | SD |
|---|---|---|---|
| 1 | 0 | 1588 | 21 |
| 2 | 11.5 | 736 | 28 |
| 3 | 11.5 | 729 | 29 |
| 4 | 4 | 1140 | 29 |
| 5 | 20 | 486 | 24 |
| 6 | 30 | 292 | 17 |

Example 10

Hormone Release Profile of Implant Containing Barium Sulphate in the Core in Comparison to Hormone Release Profile of Commercially Available Implanon (No Barium Sulfate)

In-vitro release rate profiles of the implants were tested by two methods. An accelerated release rate method was performed by testing the implant in an ethanol/water (90/10) solution. For the real time release rate method the in-vitro release profile was tested in water. For both tests the release profile of an implant containing barium sulphate in the core was compared to the profile of Implanon without barium sulphate.

Implants were manufactured loaded with 4, 20 and 30 wt % barium sulphate in the core. The resulting accelerated release profiles are shown in FIG. 13 which demonstrates that all release profiles are similar and that within the tested range of barium sulphate content of the core (0-30 wt %) the radio-opaque component does not influence the release of hormones from the device. The same conclusion can be drawn from the real time release profiles up to 76 days (FIG. 14), i.e. within the tested range of barium sulphate content of the core (0-30 wt %) the radio-opaque component does not influence the release of hormones from the device.

These conclusions were substantiated by calculating F1 values. The F1 values were calculated for both accelerated release rate profiles (up to and including 18 days) as real time release rate profiles (up to and including 76 days) taking the 0 wt % implant release profiles as reference. The results are given in Table 5. F1 values up to 15 (0-15) provide assurance of the sameness or equivalence of the two curves.

TABLE 5

F1 values for Implants loaded with 4, 20 and 30 wt % barium sulphate in the core

| Barium sulphate [wt %] | Accelerated release | Real time release |
|---|---|---|
| 4 | 4.2 | 2.9 |
| 20 | 5.8 | 6.9 |
| 30 | 6.8 | 7.5 |

Example 11

Migration of Barium Sulphate Particles Out of Implant with Open Ends

To reveal the distribution of barium sulphate in the implant and to obtain an impression of the loss of barium sulphate particles upon leaching, cryogenic sections were made of implants using a ultramicrotome. Subsequently the sections of the implants were analyzed using Scanning Electron Microscopy/Energy Dispersed Xspectroscopy (SEM/EDX) before and after leaching. Leaching the implants leads to removal of the etonogestrel crystals from the implant. By examining before and after leaching information is obtained on the morphology of the barium sulphate/etonogestrel/EVA-28 blend. A back scatter electron (BSE) detector was used for imaging. In the BSE image the presence of barium sulphate particles is easily recognized by the high brightness of the barium sulphate particles.

FIG. 15 reveals the morphology of implants in which the core is loaded with about 4, 20 and 30 wt % barium sulphate.

It can be seen that the bright spots, representing barium sulphate, are mainly located in the EVA-28 material, i.e. the irregular shaped grey/black spots, representing etonogestrel crystals, contain no bright spots. FIG. 16 reveals the same samples that were leached. The blank part is the skin material while the part containing the bright spots shows the leached core. Dark holes are clearly visible. The holes, representing the location at which etonogestrel crystals were present before leaching, hardly contain any bright spots.

The content barium sulphate in several batches was also tested using incineration before and after leaching (18 days in ethanol/water (90/10)). This gives information on possible migration of barium sulphate crystals out of the implant after the etonogestrel crystals were leached out of the implant. The results (table 6) show that there is no major change in content of barium sulphate upon leaching. It can therefore be concluded that no or hardly any barium sulphate crystals migrated out of the implant through the open ends.

By combining FIGS. 15 and 16 with the results in Table 6 it can be concluded that hardly any radio-opaque component (shown by the bright spots) was encapsulated by the hormone crystals and that most of the radio-opaque component was encapsulated by the polymer EVA-28.

TABLE 6

Remnant content $BaSO_4$ of implants (average is given and range of 6 samples is given in brackets)

| Batch | Untreated [mg $BaSO_4$/ implant] | Leached (18 days $EtOH/H_2O$) [mg $BaSO_4$/implant] |
|---|---|---|
| Core with 4 wt % $BaSO_4$ | 5.0 (4.9-5.1) | 5.6 (5.5-5.6) |
| Core with 20 wt % $BaSO_4$ | 26.2 (26.0-26.3) | 26.8 (26.6-26.9) |
| Core with 30 wt % $BaSO_4$ | 45.6 (45.4-45.8) | 45.2 (45.1-45.4) |

The invention claimed is:

1. A drug delivery device for subdermal administration of a contraceptive or hormone replacement therapy comprising (i) a core comprising (a) crystalline desogestrel or 3-ketodesogestrel; (b) a thermoplastic polymer, wherein the percent weight of the thermoplastic polymer in the core is equal to or less than the percent weight of the desogestrel or 3-ketodesogestrel; and (c) about 4-30% by weight of a radio-opaque material, wherein substantially all the radio-opaque material is encapsulated in the thermoplastic polymer and not in the crystalline desogestrel or 3-ketodesogestrel; and (ii) a non-medicated thermoplastic polymer skin covering the core.

2. The drug delivery device according to claim 1, wherein the radio-opaque material is about 6-20% by weight.

3. The drug delivery device according to claim 1, wherein the radio-opaque material is about 8-15% by weight.

4. The drug delivery device according to claim 1, wherein the radio-opaque material is barium sulphate.

5. The drug delivery device according to claim 1, wherein the device is an implant.

6. The drug delivery device according to claim 1, wherein the thermoplastic polymer in the core is ethylene-vinylacetate copolymer.

7. The drug delivery device of claim 4, wherein the barium sulphate is about 8-15% by weight.

8. An implant consisting of a coaxial rod, the rod containing (i) a core comprising (a) crystalline desogestrel or 3-ketodesogestrel, (b) an ethylene-vinylacetate copolymer having a vinylacetate content of about 28%, wherein the percent weight of the ethylene-vinylacetate copolymer is equal to or less than the percent weight of the desogestrel or 3-ketodesogestrel, and (c) about 4-30% by weight of a radio-opaque material, wherein substantially all the radio-opaque material is encapsulated in the ethylene-vinylacetate copolymer; and (ii) a non-medicated ethylene-vinylacetate copolymer skin having a vinylacetate content of about 14%, covering the core.

9. The implant of claim 8, wherein the radio-opaque material is barium sulphate.

10. The implant of claim 9, wherein the barium sulphate is about 8-15% by weight.

11. The implant of claim 8, wherein the rod has open ends.

12. The implant of claim 8, wherein the implant has a length of 40 mm and a diameter of 2 mm.

13. The implant of claim 8, wherein the amount of 3-ketodesogestrel is 68 mg.

14. A kit comprising:
a) the drug delivery device according to claim 4; and
b) an acrylonitrile-butadiene-styrene polymer applicator for inserting the implant.

15. A kit comprising:
a) the implant according to claim 9; and
b) an acrylonitrile-butadiene-styrene polymer applicator for inserting the implant.

16. An implant having a length of 40 mm and a diameter of 2 mm consisting of a coaxial rod, the rod comprising (i) a core comprising (a) 68 mg of crystalline 3-ketodesogestrel; (b) an ethylene-vinylacetate copolymer having a vinylacetate content of about 28%, wherein the percent weight of the ethylene-vinylacetate copolymer is equal to or less than the percent weight of the 3-ketodesogestrel; and (c) about 8-15% by weight of barium sulphate, wherein substantially all the radio-opaque material is encapsulated in the ethylene-vinylacetate copolymer; and (ii) a non-medicated ethylene-vinylacetate copolymer skin having a vinylacetate content of about 14% covering the core.

17. The implant of claim 16, wherein the rod has open ends.

18. A kit comprising (a) the implant according to claim 16, and (b) an acrylonitrile-butadiene-styrene polymer applicator consisting of a body, a plunger, a stainless steel needle and a polypropylene shield.

19. A drug delivery device for subdermal administration of a contraceptive or hormone replacement therapy comprising (i) a core comprising (a) crystalline desogestrel or 3-ketodesogestrel; (b) less than 50% by weight of a thermoplastic polymer; and (c) about 4-30% by weight radio-opaque material and substantially all the radio-opaque material is encapsulated in the thermoplastic polymer and (ii) a non-medicated thermoplastic polymer skin covering the core.

20. The drug delivery device according to claim 19, wherein the radio-opaque material is about 6-20% by weight.

21. The drug delivery device according to claim 19, wherein the radio-opaque material is about 8-15% by weight.

22. The drug delivery device according to claim 19, wherein the radio-opaque material is barium sulphate.

23. The drug delivery device according to claim 19, wherein the device is an implant.

24. The drug delivery device according to claim 19, wherein the thermoplastic polymer in the core is ethylene-vinylacetate copolymer.

* * * * *

UNITED STATES PATENT AND TRADEMARK OFFICE
CERTIFICATE OF CORRECTION

| | | |
|---|---|---|
| PATENT NO. | : 8,722,037 B2 | Page 1 of 1 |
| APPLICATION NO. | : 10/592725 | |
| DATED | : May 13, 2014 | |
| INVENTOR(S) | : Veenstra et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 928 days.

Signed and Sealed this
Eighteenth Day of November, 2014

Michelle K. Lee
*Deputy Director of the United States Patent and Trademark Office*